United States Patent [19]

Edwards

[11] Patent Number: 5,057,627

[45] Date of Patent: * Oct. 15, 1991

[54] ALKOXYLATION PROCESS CATALYZED BY PHOSPHATE SALTS OF THE RARE EARTH ELEMENTS

[75] Inventor: Charles L. Edwards, Houston, Tex.

[73] Assignee: Shell Oil Company, Houston, Tex.

[*] Notice: The portion of the term of this patent subsequent to Oct. 15, 2008 has been disclaimed.

[21] Appl. No.: 482,379

[22] Filed: Feb. 20, 1990

Related U.S. Application Data

[63] Continuation-in-part of Ser. No. 226,164, Jul. 29, 1988, abandoned, and a continuation-in-part of Ser. No. 204,329, Jun. 9, 1988, abandoned, and a continuation-in-part of Ser. No. 215,653, Jul. 6, 1988, abandoned.

[51] Int. Cl.$^5$ .............................................. C07C 41/03
[52] U.S. Cl. ................................ 568/618; 568/608; 568/620; 568/45; 568/55; 568/678; 568/679; 260/410.6; 560/93; 560/201; 560/200; 560/105; 560/112; 560/240; 564/399; 564/475; 564/505; 530/217; 530/230; 530/232

[58] Field of Search ............... 568/618, 620, 608, 45, 568/55, 678, 679; 260/410.6; 560/93, 209, 200, 105, 112, 240; 564/399, 475, 505; 530/217, 230, 232

[56] References Cited

U.S. PATENT DOCUMENTS 4,528,364 7/1985 Prier ..................................... 528/370
4,658,065 4/1987 Aoshima et al. ..................... 564/487

OTHER PUBLICATIONS

Y. Zhang, Inorganica Chemica Acta, 155 (1989) 263–265.

Primary Examiner—Howard T. Mars
Attorney, Agent, or Firm—Pamela J. McCollough

[57] ABSTRACT

Alkylene oxide adducts of organic compounds having active hydrogen atoms are prepared by a process which comprises contacting and reacting an alkylene oxide reactant comprising one or more vicinal alkylene oxides with an active hydrogen containing reactant comprising one or more compounds having active hydrogen atoms in the presence of a catalytically effective amount of one or more of the phosphate salts of the rare earth elements. The product alkoxylates are known to be useful, for instance, as nonionic surfactants, wetting and emulsifying agents, solvents, and chemical intermediates.

45 Claims, No Drawings

ALKOXYLATION PROCESS CATALYZED BY PHOSPHATE SALTS OF THE RARE EARTH ELEMENTS

This is a continuation-in-part of the application Ser. No. 07/226,164, filed July 29, 1988, the application Ser. No. 07/204,329, filed June 9, 1988, and the application Ser. No. 07/215,653, filed July 6, 1988 all abandoned.

BACKGROUND OF THE INVENTION

This invention relates to an alkoxylation process in which alkylene oxides are reacted with compounds having active hydrogen atoms in the presence of catalysts comprising one or more phosphate salts of the rare earth elements. In particularly preferred embodiments, the invention relates to processes for the preparation of alkoxylate products useful as nonionic surfactants.

A large variety of products useful, for instance, as nonionic surfactants, wetting and emulsifying agents, solvents, and chemical intermediates, are prepared by the addition reaction (alkoxylation reaction) of alkylene oxides (epoxides) with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of commercial cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula 11) to a single alkanol molecule (formula I) is presented by the equation

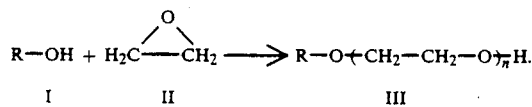

The present invention particularly relates to an alkoxylation reaction catalyzed by the phosphate salts of one or more of the rare earth elements.

Conventional alkoxylation catalysts include the basic salts of the alkali metals of Group I of the Periodic Table, e.g., sodium, potassium, rubidium, and cesium, and the basic salts of certain of the alkaline earth metals of Group II of the Periodic Table, e.g., calcium, strontium, barium and in some cases magnesium. Conventional acidic alkoxylation catalysts include, broadly, the Lewis acid or Friedel-Crafts catalysts. Specific examples of these acid catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines has also been reported. Still other examples of known acidic alkoxylation catalysts are sulfuric and phosphoric acids; perchloric acid and the perchlorates of magnesium, calcium, manganese, nickel and zinc; certain metal oxalates, sulfates, phosphates, carboxylates and acetates; alkali metal fluoroborates; zinc titanate, and certain metal salts of benzene sulfonic acid. Other art on the subject of alkoxylation includes U.S. Pat. No. 4,727,199, which describes a process for reacting a liquid or solid alkylene oxide with a liquid or gaseous active hydrogen compound in the presence of a catalytic amount of an anion-bound metal oxide heterogeneous catalyst, wherein the anion is $SO_4$, $BF_4$, $CO_3$, $BO_3$, $PO_4$, $SeO_4$ $MoO_4$, $B_4O_7$ or $PF_6$ and the metal oxide is an oxide of zirconium, nickel, aluminum, tin, calcium, magnesium, iron, titanium, thorium, hafnium, or rubidium. Still other prior art describes the use of zeolitic materials as alkoxylation catalysts, while European patent application 0250168 and other art cited therein disclose lamellar clay catalysts.

Alkylene oxide addition reactions are known to produce a product mixture of various alkoxylate molecules having different numbers of alkylene oxide adducts (oxyalkylene adducts), e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service. The present invention provides a process characterized by enhanced selectivity for the preparation of alkoxylate mixtures in which a relatively large proportion of the alkoxylate molecules have a number (n) of alkylene oxide adducts that is within a relatively narrow range of values.

It is known in the art that alcohol alkoxylate products having a narrow range alkylene oxide adduct distribution are preferred for use in certain detergent formulations (Great Britain Patent No. 1,462,134; Derwent Publications Research Disclosure number 194,010). Narrow-range alcohol alkoxylates are also known to be particularly valuable as chemical intermediates in the synthesis of certain carboxyalkylated alkyl polyethers (U.S. Pat. No. 4,098,818) and of certain alkyl ether sulfates (Great Britain Patent No. 1,553,561). Conventional commercial alkoxylate preparation, which has in large part been limited to the use of basic catalysts, particularly the metals sodium and potassium and their oxides and hydroxides, yields only a relatively broad distribution range product. Conventional acid-catalyzed alkoxylation reactions have long been known to produce a more narrow range product than that obtained with the alkali metal catalysts. However, acid catalysts have substantial disadvantage in several other respects. For instance, the acids are often unstable with limited life and effectiveness as catalysts in the alkoxylation mixture. Both the acid catalysts themselves and their decomposition products catalyze side reactions producing relatively large amounts of polyalkylene glycols, and also react directly with the components of the alkoxylation mixture to yield undesirable, and often unacceptable, by-products such as organic derivatives of the acids.

Also of substantial importance in alkoxylation processes is the ability of the process to minimize the quantity of unreacted (or residual) active hydrogen reactant remaining in the final product. A high level of residual reactant either represents a loss of valuable reactant, or requires that further processing of the product be carried out to recover the reactant. Moreover, the presence of the unreacted material is often of disadvantage from the standpoint of product quality and environmental concerns. For instance, residual alkanol in a detergent alcohol ethoxylate product contributes to volatile organic emissions during spray drying of detergent formulations.

It has recently been reported in the art that, in addition to conventional acidic catalysts, a number of other substances have been found to function as catalysts or in co-catalyst combinations which are capable of producing relatively narrow distributions for the oxyalkylene adducts of higher alkanols and other active hydrogen containing compounds. For instance, it has recently been disclosed (U.S. Pat. No. 4,306,093 and and U.S. Pat. No. 4,239,917, and published European Patent Applications 0026544, 0026546, 0026547 and that certain compounds of barium, strontium, and calcium promote narrow-range alkoxylation products. U.S. Pat. No. 4,210,764 and U.S. Pat. No. 4,223,164 describe the use of cresylic acids to promote alkoxylation catalyzed by barium and strontium compounds. U.S. Pat. No. 4,302,613 reports that a more peaked reaction product can be obtained by combining barium and strontium alkoxylation catalysts with co-catalysts such as calcium oxide, calcium carbide, calcium hydroxide, magnesium metal, magnesium hydroxide, zinc oxide and aluminum metal. U.S. Pat. No. 4,453,023 describes a process for preparing alkoxylates having a narrower molecular weight distribution which employs a catalyst comprising a barium compound and a promoter selected from the class consisting of superphosphoric acid, phosphoric acid, diphosphoric acid, triphosphoric acid, phosphorus acid, dihydrogen phosphate compounds, oxides of phosphorus, carbon dioxide, and oxalic acid. U.S. Pat. No. 4,453,022 describes a similar process wherein the catalyst comprises a calcium or strontium compound and a promoter selected from the class consisting of superphosphoric acid, phosphoric acid, diphosphoric acid, triphosphoric acid, phosphorus acid, dihydrogen phosphate compounds, oxides of phosphorus, sulfuric acid, bisulfate compounds, carbonic acid, bicarbonate compounds, carbon dioxide, oxalic acid and oxalic acid salts, sulfur trioxide, sulfur dioxide, and sulfurous acid. Published PCT application WO 85/00365 discloses other activated calcium containing alkoxylation catalysts capable of producing narrow range alkoxylation products. U.S. Pat. No. 4,375,564 reports that a narrow range product results from alkoxylation reactions catalyzed by a magnesium compound in combination with a compound of one of the elements aluminum, boron, zinc, titanium, silicon, molybdenum, vanadium, gallium, germanium, yttrium, zirconium, niobium, cadmium, indium, tin, antimony, tungsten, hafnium, tantalum, thallium, lead and bismuth. U.S. Pat. No. 4,483,941 discloses catalysts for alkoxylation reactions which comprise either $BF_3$ or $SiF_4$ in combination with an alkyl or alkoxide compound of aluminum, gallium, indium, thallium, titanium, zirconium, and hafnium. U.S. Pat. No. 4,456,697 describes an alkoxylation catalyst which comprises a mixture of HF and one or more metal alkoxides. Japanese patent specification 52051307 to Tokuyama Soda KK discloses the selective preparation of mono- rather than di- or tri-alkylene glycol esters from alkylene oxide and alcohol using solid acid catalysts such as silica, alumina, titania, vanadium pentoxide, antimony pentoxide, titanyl sulfate, tungstic acid, phosphotungstic acid, and silver perchlorite.

Recently issued U.S. Pat. No. 4,721,816 claims a process for preparing narrow range distribution alkoxylates, wherein the catalyst is a combination of one or more sulfur-containing acids with one or more aluminum alcoholate or phenolate compounds. U.S. Pat. No. 4,721,817 claims a similar process wherein the combination contains one or more phosphorus-containing acids.

U.S. Pat. No. 4,665,236 and U.S. Pat. No. 4,689,435 describe a process for the alkoxylation of active hydrogen reactants using certain metal oxo alkoxide catalysts. With regard to the use in this invention of catalysts comprising one or more phosphate salts of the rare earth elements, the catalysts described in these patents include compounds in which one of the metal species in the bimetallic molecule is a rare earth element.

The aforementioned European application 0250168 discloses lamellar clay catalysts which have been ion exchanged with rare earths. With regard to the use in this invention of phosphate salt catalysts, prior art uses of phosphoric acid and phosphate salts as alkoxylation catalysts have not involved compounds of or other combinations with the rare earth elements.

SUMMARY OF THE INVENTION

It has now been found that phosphate salt compounds of the rare earth elements are effective catalysts for the addition reactions of alkylene oxides with organic compounds having active hydrogen atoms. It has further been found that, in certain preferred embodiments, an alkoxylation reaction catalyzed by a rare earth phosphate provides an alkoxylate product, particularly an alkanol ethoxylate product, of exceptionally narrow-range alkylene oxide adduct distribution.

The present invention is particularly directed to a process for the preparation of alkoxylates of active hydrogen containing organic compounds which comprises contacting an alkylene oxide reactant comprising one or more vicinal alkylene oxides with an active hydrogen reactant comprising one or more organic compounds (e.g., alcohols, phenols, thiols, amines, polyols, carboxylic acids, etc.) having one or more active hydrogen atoms, in the presence of a catalyst comprising one or more of the phosphate salts of the rare earth elements.

As the terminology is used herein, the "rare earth" elements are those of atomic numbers 39 and 57 through 71, elements of the "lanthanum series" are those of atomic numbers 57 through 71; the "lanthanide" elements are those of atomic numbers 58 through 71. Traditionally, the lanthanum series has further been divided into the "cerium earth" group of atomic numbers 57 through 62, the "terbium earth" group of atomic numbers 63 through 66, and the "yttrium earth" group of atomic numbers 67 through 71 (so named not because yttrium is a member of the group, but because yttrium is found with these elements in nature).

In general terms, the catalyst for the process of the invention comprises one or more of the phosphate salts of the rare earth metals. In one preferred embodiment, the catalyst comprises one or more of the phosphate salts of the lanthanum series elements. In another embodiment, the catalyst comprises one or more of the phosphate salts of the lanthanide elements. In a further specific embodiment, the catalyst comprises one or more of the phosphate salts of the elements of the cerium earth group. In still another specific embodiment, the catalyst comprises a mixture of rare earth metal phosphate salts wherein the distribution of the rare earth elements substantially corresponds to that of a naturally occurring rare earth ore, for example, monazite, bastnasite, xenotime, gadolinite or euxenite.

The rare earth phosphate salts are present in the alkoxylation mixture in catalytically effective amount in either (or both) homogeneous or heterogeneous form(s). The catalyst has been found to heterogeneous, or at least essentially heterogeneous, in preferred embodiments.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are well known in the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more vicinal alkylene oxides, particularly the lower alkylene oxides and more particularly those in the $C_2$ to $C_4$ range. In general, the alkylene oxides are represented by the formula

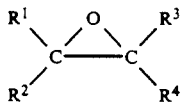

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide and propylene oxide. Alkylene oxide reactants consisting essentially of ethylene oxide are considered most preferred from the standpoint of commercial opportunities for the practice of alkoxylation processes, and also from the standpoint of the preparation of products having narrow-range ethylene oxide adduct distributions.

Likewise, the active hydrogen reactants suitably utilized in the process of the invention include those known in the art for reaction with alkylene oxides and conversion to alkoxylate products. Suitable classes of active hydrogen reactants include (but are not necessarily limited to) alcohols, phenols, thiols (mercaptans), amines, polyols, carboxylic acids, and mixtures thereof. It is generally, but not necessarily, the case that the active hydrogen moiety of the reactant is of the form —XH wherein X represents either an oxygen, sulfur or (substituted, e.g., amino) nitrogen atom. Preference generally exists for use of hydroxyl-containing reactants. More preferably, the active hydrogen-containing reactant consists essentially of one or more active hydrogen containing compounds selected from the group consisting of alkanols, alkyl polyols and phenols (including alkyl-substituted phenols).

Preference can also be expressed for the application of this invention to the alkoxylation of primary active hydrogen containing compounds, that is, compounds wherein the wherein the active hydrogen moiety is attached to a primary carbon atom. As is often the case for alkoxylation reactions, such primary compounds are more reactive, and in some cases substantially more reactive, in the process of this invention than are the corresponding secondary and tertiary compounds. Moreover, the invention has been found to produce relatively broad-range alkylene oxide adduct distribution products when applied to secondary and tertiary active hydrogen containing reactants.

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, steric acid, oleic acid, rosin acids, tall oil acids, terephthalic acid, benzoic acid, phenylacetic acid, toluic acid, acrylic acid, methacrylic acid, crotonic acid, maleic acid, and the like. It has been observed that, as a rule, carboxylic acids undergo alkoxylation in the process of this invention at a relatively slow rate.

Among the suitable amines, particular mention may be made of primary, secondary and tertiary alkylamines and of alkylamines containing both amino and hydroxyl groups, e.g., N'N-di(n-butyl)-ethanol amine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

Among the polyols, particular mention may be made of those having from 2 to about 6 hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like.

The alcohols (both mono- and poly-hydroxy) and the phenols (including alkyl-substituted phenols)are preferred classes of active hydrogen reactants for purposes of the invention. Among the phenols, particular mention may be made of phenol and of alkyl-substituted phenols wherein each alkyl substituent has from one to about 30 (preferably from one to about 20)carbon atoms, for example, p-methylphenol, p-ethylphenol, p-hexylphenol, nonylphenol, p-decylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to about 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than about 50 percent, more preferably greater than about 60 percent and most preferably greater than about 70 percent of the molecules are of linear (straight-chain) carbon structure.

The general suitability of such alkanols as reactants in alkoxylation reactions is well recognized in the art. Commercially available mixtures of primary mono-hydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Proctor and Gamble Company and the TA alcohols of Ashland Oil Company.

Among the polyols, particular mention may be made of those having from 2 to about 6 hydroxyl groups and 2 or more, preferably 2 to 30 carbon atoms. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like. Higher oligomers and polymers of the polyols are also very suitable.

The active hydrogen containing reactant is also very suitably the alkoxylate product of a previous alkoxylation of an active hydrogen containing compound.

Further examples of both specific alkylene oxide reactants and specific active hydrogen containing reactants suitable for use in this invention are recited in the aforementioned U.S. Patents, the relevant disclosures of which are incorporated herein by this reference.

For purposes of the invention, the alkylene oxide reactant and the active hydrogen reactant are necessarily contacted in the presence of a catalyst comprising one or more of the phosphate salts of the rare earth elements. The catalyst is applied in a quantity which is effective to catalyze the alkoxylation reaction.

The catalyst in a given application of this process suitably contains the phosphate salt(s) of either one or a mixture of the rare earth elements. In one respect, preference can be expressed for catalysts comprising in catalytically effective amount one or more of the phosphate salts of elements selected from the group comprising cerium, lanthanum, praseodymium, neodymium, yttrium, samarium, gadolinium, dysprosium, erbium, and ytterbium. In another respect, catalysts comprising a catalytically effective amount of one or more of the phosphate salts of the cerium earth group elements are particularly preferred, while catalysts comprising a catalytically effective amount of one or more of the phosphate salts of elements selected from the group consisting of cerium and lanthanum are considered most preferred. In a further respect, preferred catalysts comprise a catalytically effective amount of one or more of the phosphate salts of the lanthanum elements (atomic numbers 57–71). Still further, a preferred class of catalysts comprise a catalytically effective amount of one or more of the phosphate salts of the lanthanide series elements (atomic numbers 58–71). In still another respect, preference can be expressed for catalysts comprising yttrium phosphate in catalytically effective amounts.

Natural mineral ores which serve as the commercial sources of the rare earth elements generally contain several of the elements. These ores are often refined without separating this mixture into distinct elements. For this reason, the use in the invention of mixtures of the phosphate salts of several rare earth elements may be preferred from the standpoint of availability and cost. Specific examples of suitable mixtures of rare earth elements include those known as bastnasite, monazite, xenotime, didymium, gadolinite and euxenite.

In addition to a catalytically effective amount of the rare earth element compounds, the catalyst for the process of the invention may also suitably contain other substances, including both those which may be introduced into the process as impurities in the phosphate salt catalyst as well as those which may be added to promote or modify catalyst activity.

The one or more of the phosphate salts of the rare earth elements are present in the reaction mixture in a catalytically effective amount, i.e., an amount sufficient to promote the alkoxylation reaction or influence the alkylene oxide adduct distribution of the product. Although a specific quantity of catalyst is not critical to the invention, preference may be expressed for use of the catalyst in amount of at least about 0.01 percent by weight (% w), while an amount between about 0.02 and 5% w is considered more preferred and an amount between about 0.1 and 2% w is considered most preferred for typical embodiments. These percentages are in terms of the weight of rare earth metal ions in the process mixture relative to the weight of active hydrogen containing compounds in that mixture. Substantially greater quantities of catalyst, e.g., up to about 10% w or more, are also very suitable. As a rule, the higher the desired average alkylene oxide adduct number of the alkoxylate product and the higher the desired rate of reaction, the greater the required quantity of catalyst.

The phosphate salt catalyst for this invention is suitably either added per se to the alkoxylation process or formed in situ in the process mixture. With respect to in situ catalyst formation, it has been found very suitable to utilize as catalyst a combination of one or more other rare earth element compounds with a phosphoric acid, particularly orthophosphoric acid.

The phosphate salt catalyst compounds are suitably characterized by the formula $L_p - (PO_4)_q$, wherein L is a rare earth element. As is well recognized in the art, the phosphate salts of the rare earth elements principally comprise rare earth elements in the trivalent state and have the formula $LPO_4$. However, the invention is also intended to encompass divalent metal salts and tetravalent metal salts, in which case the subscripts p and q satisfy the relevant valency relationships, that is, when L is divalent p is 3 and q is 2, and when L is tetravalent p is 3 and q is 4. It is to be expected that generally the phosphate sale catalyst as prepared and as used in the invention will consist essentially of compounds of the formula $LPO_4$.

In preferred embodiments, the alkylene oxide reactant is ethylene oxide or propylene oxide or a mixture of ethylene oxide and propylene oxide and the active hydrogen containing reactant is an alcohol, a polyol or another hydroxyl containing compound in the presence of a catalytically effective amount of the rare earth phosphate salt catalyst. In a particularly preferred embodiment, ethylene oxide is contacted and reacted with a $C_1$ to $C_{30}$ primary alkanol in the presence of a catalytically effective amount of a catalyst wherein the rare earth phosphate compounds consist essentially of salts having the formula $LPO_4$.

In terms of processing procedures, the alkoxylation reaction in the invention may be conducted in a generally conventional manner. For example, the catalyst may initially be mixed with liquid active hydrogen reactant. The mixture of catalyst and liquid reactant is contacted, preferably under agitation, with alkylene oxide reactant, which is typically introduced in gaseous form, at least for the lower alkylene oxides. The order in which the reactants and catalyst are contacted has not been found to be critical to the invention.

While these procedures describe a batch mode of operation, the invention is equally applicable to a continuous process.

The catalyst is either soluble (either partially or completely) or insoluble in this liquid reactant as well as in liquid mixtures of the reactant and the product formed as the process is carried out. The catalyst is insoluble, or at least essentially insoluble, in the preferred active hydrogen containing reactants, particularly in primary alcohols and the products of their alkoxylation. While it is not intended to limit the scope of the invention to one theory or mechanism of operation, it is believed that the presence of phosphate salts in a hexagonal crystal structure in the alkoxylation mixture, particularly in alkanol alkoxylation mixtures, may have a beneficial influence on reaction rate and adduct distribution. Salts in the monoclinic form have been observed in some cases to be less active than the salts in the hexagonal form. Preference has also been observed for use of phosphate salts having a certain water content associated with their crystal structure, particularly a water content of greater than about 5% w (e.g., 5-20% w), although the amount of water contained in the phosphate salt is not considered critical to this invention.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Superatmospheric pressures, e.g., pressures between about 10 and 150 psig, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments is in the range from 1 to 24 hours.

After the ethoxylation reaction has been completed, the product is preferably cooled. If desired, catalyst can be removed from the final product, although catalyst removal is not necessary to the process of the invention. Catalyst residues may be removed, for example, by filtration, precipitation, extraction, or the like. A number of specific chemical and physical treatment methods have been found to facilitate removal of catalyst residues from a liquid product. Such treatments include contact of the alkoxylation product with strong acids such as phosphoric and/or oxalic acids or with solid organic acids such as NAFION H+ or AMBERLITE IR 120H; contact with alkali metal carbonates and bicarbonates; contact with zeolites such as Type Y zeolite or mordenite; or contact with certain clays. Typically, such treatments are followed by filtration or precipitation of the solids from the product. In many cases filtration, precipitation, centrifugation, or the like, is most efficient at elevated temperature.

Alkoxylation product mixtures prepared under the present invention are of high quality and have greater stability, relative to the product mixtures of acid or base catalyzed alkoxylation reactions. In this regard, the invention is particularly useful for the preparation of colorless or less colored product relative to those of conventional practice, because the neutral salts do not promote degradation reactions which lead to color forming impurities.

The following Examples are provided to further illustrate certain specific aspects of the invention but are not intended to limit its broader scope.

EXAMPLE 1

A lanthanum phosphate compound was prepared by the following procedures. A first solution was prepared by dissolving 10 grams of $LaCl_3 \cdot 6H_2O$ in 200 grams of deionized water. A second solution was prepared by dissolving 10.64 grams of sodium orthophosphate ($Na_3PO_4 \cdot 12H_2O$) 12H2O) in 200 grams of water. The first solution (at room temperature) was added dropwise over a period of 25 minutes to the second solution (at 50° C.), The resulting mixture was stirred for an additional 30 minutes at 50° C., and then filtered hot to separate a white precipitate. The filter cake was washed three times with 100 ml of 50° C. deionized water. After drying, 7.4 grams of solid was recovered as a powder.

An alkoxylation process in accordance with the invention was conducted under the following procedures. The alkylene oxide reactant for this process embodiment consisted of ethylene oxide and the active hydrogen containing reactant consisted of NEODOL 23 Alcohol (NEODOL is a trademark of Shell Chemical Company) characterized as a mixture of primary, 80% linear (20% branched), alkanols having twelve and thirteen carbon atoms (about 40% by mol $C_{12}$ and 60% by mol $C_{13}$).

Initially, 3.0 grams of the powder prepared as described above was added to 200 grams of NEODOL 23 Alcohol, and the mixture was heated to 130° C. under nitrogen sparge for 3 hours to drive off water. The resulting slurry was transferred to a one-liter autoclave reactor maintained under nitrogen atmosphere. The temperature of the reactor and contents was raised to 140° C. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied on demand to maintain an essentially constant 75 psia pressure. Temperature was maintained at 140° C. A total of 315 grams of ethylene oxide was taken up over a period of 2.5 hours. The reactor was maintained for an additional 1 hour to consume unreacted ethylene oxide in the system.

The product was analyzed by GC-LC techniques and found to have a mean average adduct number of 6.6. The ethylene oxide adduct distribution of the product is presented in the following table. The only observed by-products were polyethylene glycols (PEG) in a quantity of 2.0% w.

| ETHOXYLATE DISTRIBUTION | |
|---|---|
| Adduct Number | Concentration |
| 0 (Residual Alcohol) | 1.9% w |
| 1 | 0.8 |
| 2 | 0.8 |
| 3 | 1.3 |
| 4 | 3.6 |
| 5 | 10.0 |
| 6 | 18.4 |
| 7 | 22.3 |
| 8 | 17.6 |
| 9 | 10.4 |
| 10 | 5.4 |
| 11 | 2.9 |
| 12 | 1.5 |
| 13 | 1.0 |
| 14 | 0.7 |
| 15 | 0.5 |
| 16 | 0.4 |
| 17 | 0.4 |
| 18 | 0.3 |

EXAMPLE 2

A catalyst was prepared according to the following procedure. A total of 10.9 grams of $Ce(NO_3)_3 \cdot 6H_2O$ was dissolved in 100 grams of deionized water and this solution was heated to 60° C. A solution formed by dissolving 3 grams of 85% w $H_3PO_4$ in 10 grams of deionized water was added to the aqueous cerium nitrate solution. The total solution was stirred for an additional hour at 80° C. The resulting mixture, which contained a fine white solid, was cooled to 25° C, and the solid was isolated and washed free of any residual acid. After drying under vacuum at 50° C., a total of 5.8 grams of a free flowing, off-white powder was obtained.

One gram of this powder was added to 195 grams of the NEODOL 23 Alcohol, and the mixture was heated to 130° C. under nitrogen sparge for 2 hours to drive off water. The resulting mixture was transferred to an autoclave reactor and the alcohol ethoxylated at 140° C. and at a pressure of 80 psia (30 psia ethylene oxide and 50 psia nitrogen). A total of 309 grams of ethylene oxide was consumed over a period of 2 hours, yielding a product having a mean average adduct number of 6.8. The adduct distribution of this product is presented in the following table.

| ETHOXYLATE DISTRIBUTION | |
|---|---|
| Adduct Number | Concentration |
| 0 (Residual Alcohol) | 1.4% w |
| 1 | 0.5 |
| 2 | 0.6 |
| 3 | 1.0 |
| 4 | 2.7 |
| 5 | 8.5 |
| 6 | 18.4 |
| 7 | 24.4 |
| 8 | 20.3 |
| 9 | 11.9 |
| 10 | 5.6 |
| 11 | 2.5 |
| 12 | 1.2 |
| 13 | 0.6 |
| 14 | 0.4 |
| 15 | 0.2 |

EXAMPLE 3

A catalyst was prepared under the following procedure. A total of 0.99 gram of 85%w $H_3PO_4$ dissolved in 14 grams of deionized water was added to a suspension of 8.5 grams of praseodymium oxide ($Pr_6O_{11}$) in 140 grams of deionized water, heated to 60° C. The resulting mixture was stirred for an additional hour at 80° C. A solid product formed and was isolated by filtration and washed several times with deionized water until the washings were neutral to pH paper. The reddish-brown solid was dried in vacuo at 80° C. producing 8.8 grams of a fine, free-flowing powder.

Three grams of this powder was added to 200 grams of NEODOL 23 Alcohol. An ethoxylation reaction was then carried out according to the procedures described in Example 2. A total of 318 grams of ethylene oxide was consumed over a 2 hour period at a reaction temperature of 155° C. The product had a mean average adduct number of 6.6. The adduct distribution of this product is presented in the following table.

| ETHOXYLATE DISTRIBUTION | |
| --- | --- |
| Adduct Number | Concentration |
| 0 (Residual Alcohol) | 2.0% w |
| 1 | 0.6 |
| 2 | 0.6 |
| 3 | 1.3 |
| 4 | 3.7 |
| 5 | 10.1 |
| 6 | 18.6 |
| 7 | 21.4 |
| 8 | 17.0 |
| 9 | 10.5 |
| 10 | 8.8 |
| 11 | 3.2 |
| 12 | 1.8 |
| 13 | 1.1 |
| 14 | 0.8 |
| 15 | 0.5 |
| 16 | 0.4 |
| 17 | 0.3 |
| 18 | 0.2 |

EXAMPLE 4

A catalyst was prepared according to the procedures described in Example 21, except that 5.94 grams of 85% w $H_3PO_4$ was used instead of 0.99 gram. (This represented a molar ratio of $H_3PO_4$ to $Pr_6O_{11}$ of 6:1 instead of 1:1 as in Example 3.) The catalyst was isolated in the same manner and used directly in ethoxylation. Three grams of the catalyst was added to 197 grams of NEODOL 23 Alcohol and the alcohol was ethoxylated under the conditions described in Example 2. A total of 312 grams of ethylene oxide was consumed over a 3 hour period. The average adduct number of the product was 6.9. The adduct distribution of the product is presented in the following table.

| ETHOXYLATE DISTRIBUTION | |
| --- | --- |
| Adduct Number | Concentration |
| 0 (Residual Alcohol) | 1.3% w |
| 1 | 0.5 |
| 2 | 0.5 |
| 3 | 0.9 |
| 4 | 2.4 |
| 5 | 7.2 |
| 6 | 16.5 |
| 7 | 23.5 |
| 8 | 22.1 |
| 9 | 13.9 |
| 10 | 6.7 |
| 11 | 2.7 |
| 12 | 1.1 |
| 13 | 0.5 |
| 14 | 0.2 |
| 15 | 0.1 |

EXAMPLE 5

A catalyst was prepared according to the general procedures of Example 3 using a rare earth mixture obtained from Molycorp, Inc. The mixture was a rare earth hydroxychloride having a distribution of rare earth metals: 15% w Ce, 57%w La, 20% w Nd and 8%w Pr, each in the form of its hydroxychloride salt. A solution of 3 grams of 85% w $H_3PO_4$ in 14 grams of deionized water was added to a suspension of 5.2 grams of the rare earth hydroxychloride mixture in 140 grams of deionized water heated to 60° C. The catalyst was prepared as described following the general procedures of Example 21 and isolated by centrifugation. The recovered solid was washed several times with deionized water to remove traces of residual phosphoric acid. The solid was dried in vacuo at 80° C., and a total of 6.15 grams was isolated as a free flowing, off-white powder.

One gram of this powder was added to 195 grams of NEODOL 23 Alcohol, and the mixture was then dried at 130° C. under nitrogen sparge to remove water. The alcohol was ethoxylated under the same procedures as described in Example 2. A total of 310 grams ethylene oxide was consumed over 80 minutes. The product was determined to have an average adduct number of 7.0. The adduct distribution of the product is presented in the following table.

| ETHOXYLATE DISTRIBUTION | |
| --- | --- |
| Adduct Number | Concentration |
| 0 (Residual Alcohol) | 1.4% w |
| 1 | 0.5 |
| 2 | 0.4 |
| 3 | 0.9 |
| 4 | 2.4 |
| 5 | 7.5 |
| 6 | 17.0 |
| 7 | 22.3 |
| 8 | 21.2 |
| 9 | 12.9 |
| 10 | 6.7 |
| 11 | 3.1 |
| 12 | 1.9 |
| 13 | 0.8 |
| 14 | 0.5 |
| 15 | 0.3 |
| 16 | 0.2 |
| 17 | 0.1 |

EXAMPLE 6

An ethoxylation catalyst was prepared by the following procedure. A first solution was prepared by dissolving 10.4 grams of $LaCl_3 \cdot 6H_2O$ in a mixture of 200 grams of 2-ethoxyethanol and 301 grams of NEODOL 23 Alcohol. This solution was heated to 155° C and 83 grams of 2-ethoxyethanol were removed along with essentially all of the water. The solution was cooled and determined to have a water content of 79 ppm.

A second solution was prepared by dissolving 5.83 grams of 85% w potassium hydroxide in 500 grams of the alcohol. This solution was heated to 130° C. under nitrogen sparge for several hours until its water content was 175 ppm. A total of 106 grams of 2-ethoxyethanol was added to this solution, and the mixture was heated to 80° C.

The first solution was added dropwise to the second solution over a 2 hour period while maintaining a temperature of 80° C. The solution became cloudy immediately and remained a slurry. Heating was continued with stirring for an additional 14 hours. Stirring was then discontinued and the mixture filtered to remove precipitated potassium chloride.

To 242 grams of the resulting solution, analyzed to contain 0.0072 mols of lanthanum, was added dropwise over 10 minutes at 70° C, 0.816 grams of 85% w phosphoric acid. The mixture was heated an additional 30 minutes at 70° C. After heating to evaporate off essentially all 2-ethoxyethanol, the remaining solution (178 grams) was transferred to an autoclave reactor and ethoxylated at a temperature of 140° C., according to the general procedures of Example 1, for a reaction period of 90 minutes. A total of 282 grams of ethylene oxide were consumed, producing an alkanol ethoxylate having a mean average adduct number of 7.0. The adduct distribution is illustrated in the following table.

| ETHOXYLATE DISTRIBUTION | |
|---|---|
| Adduct Number | Concentration |
| 0 (Residual Alcohol) | 1.6% w |
| 1 | 0.5 |
| 2 | 0.4 |
| 3 | 0.9 |
| 4 | 2.6 |
| 5 | 7.4 |
| 6 | 15.8 |
| 7 | 22.5 |
| 8 | 20.7 |
| 9 | 13.6 |
| 10 | 6.6 |
| 11 | 3.1 |
| 12 | 1.6 |
| 13 | 0.9 |
| 14 | 0.6 |
| 15 | 0.5 |
| 16 | 0.3 |
| 17 | 0.3 |
| 18 | 0.2 |

EXAMPLE 7

The general procedures of Example 6 were repeated, substituting n-butanol for 2-ethoxyethanol. The two solutions were prepared and mixed and the precipitate filtered to produce 118 grams of a solution containing 0.0036 mols of lanthanum. A total of 0.41 grams (0.0035 mols) of 85% w H₃PO₄ was added dropwise, as the mixture was stirred for 30 minutes. After heating to evaporate off essentially all butanol, the remaining solution (101 grams) was diluted with an additional 85 grams of dry NEODOL 23 Alcohol. This solution was then transferred to an autoclave reactor and ethoxylated at a temperature of 140° C. to 155° C., according to the general procedures of Example 1, for a reaction period of 4 hours. A total of 281 grams of ethylene oxide were consumed, producing an alkanol ethoxylate having a mean average adduct number of 7.0. The adduct distribution is illustrated in the following table.

| ETHOXYLATE DISTRIBUTION | |
|---|---|
| Adduct Number | Concentration |
| 0 (Residual Alcohol) | 2.2% w |
| 1 | 0.8 |
| 2 | 0.9 |
| 3 | 1.5 |
| 4 | 3.1 |
| 5 | 6.7 |
| 6 | 12.2 |
| 7 | 17.5 |
| 8 | 18.9 |
| 9 | 15.6 |
| 10 | 10.2 |
| 11 | 5.9 |
| 12 | 2.6 |
| 13 | 1.2 |
| 14 | 0.5 |
| 15 | 0.3 |
| 16 | 0.2 |
| 17 | 0.1 |
| 18 | 0.0 |

EXAMPLE 8

A catalyst was prepared according to the following procedure. A total of 0.687 grams of a 1:1 mixture by mol of monobutyl phosphate and dibutyl phosphate was added to 110 grams of mixture containing 0.0036 mols of lanthanum in 2-ethoxyethanol and NEODOL 23 Alcohol at 70° C. with stirring. The 2-ethoxyethanol was removed via vacuum distillation leaving 92.5 grams of a catalyst mixture. This was diluted with additional alcohol producing a total weight of 185 grams. The mixture was transferred to the autoclave reactor and ethoxylated at a temperature of 170° C., according to the general procedures of Example 1, for a reaction period of 4 hours. A total of 103 grams of ethylene oxide were consumed, producing an alkanol ethoxylate having a mean average adduct number of 2.5.

EXAMPLE 9

A catalyst was prepared according to the procedures of Example 8 except that 1.58 grams of 1:1 mixture by mol of monolauryl phosphate and dilauryl phosphate was used with the mixture containing 0.0036 mols of lanthanum in 2-ethoxyethanol and NEODOL 23 Alcohol. After removal of the 2-ethoxyethanol and dilution with additional alcohol, the mixture (172 grams) was transferred to the autoclave reactor and ethoxylated at 170° C. for 4 hours. A total of 107 grams of ethylene oxide were consumed, producing an alkanol ethoxylate having a mean average adduct number of 2.6.

EXAMPLE 10

This example illustrates ethoxylation reactions of a variety of active hydrogen compounds, using a lanthanum phosphate catalyst.

The catalyst for these ethoxylation reactions was prepared by the following procedure. In a 5 liter flask, 500 grams of anhydrous lanthanum carbonate was suspended with stirring in two liters of water. This slurry was added continuously over a 30 minute period to a solution of 329 g of 85% w phosphoric acid in 2.5 liters of water in a 12 liter flask. An additional 0.5 liters of water was used to rinse the 5 liter flask and was then added to the 12 liter flask. The mixture was then heated to reflux and boiled for 2.5 hours, as carbon dioxide evolved from reaction of the carbonate with the acid. Temperature was then reduced to 80° C. and a total of 4800 ml of clear supernatant liquid was drawn off. Five liters of fresh distilled water was added to the remaining wet solid; it was resuspended and stirred at 50° C. for 30 minutes. After settling of the solid, 5 liters of liquid was drawn off and replaced with 5 liters of distilled water. 20 ml of 10N ammonium hydroxide was added dropwise over 5 minutes, and the mixture was stirred for 40 minutes. The mixture was filtered to recover solids (course powder) which was dried under nitrogen and under vacuum and ground (under nitrogen) to a fine white powder. Analysis of the product (527 grams) showed the presence of hexagonal crystals; average crystallite size was estimated to be about 200 Å.

The lanthanum phosphate thus prepared was used to catalyze several ethoxylation reactions. Each reaction was carried our according to the general procedures of Example 1. For the reaction of the Guerbet alcohol (a mixture of branched carbon chain alkanols predominantly of carbon number 16 marketed by Henkel Corp. under the trademark EUTANOL G-16), 192 grams of ethylene oxide were added to a stirred mixture of 223.75 grams of the alcohol and 0.75 grams of the lanthanum phosphate over a one hour period at a temperature of 155° C. For a first reaction of ethylene glycol, 440 grams of ethylene oxide were added to a stirred mixture of 210 grams of ethylene glycol and 11.8 grams of lanthanum phosphate over a period of three hours at 155° C. A second reaction of ethylene glycol was made under lower catalyst usage—198 grams of ethylene oxide was added to a mixture of 0.8 grams of lanthanum phosphate in 140 grams of ethylene glycol over a period of 300 minutes. The reaction of the NEODOL 23 Alcohol consumed 324 grams of ethylene oxide upon addition to a stirred mixture of 210 grams of the alcohol and 0.98 grams of the lanthanum phosphate over 70 minutes at 155° C. For the reaction of ALFOL 1412 Alcohol, 315 grams of ethylene oxide were added to a stirred mixture of 210 grams of the alcohol over a period of 70 minutes at a temperature of 155° C. For the ethoxylation of nonylphenol, ethylene oxide was added to a stirred mixture of 497 grams of the nonylphenol and 2.2 grams of the lanthanum phosphate over a period of 129 minutes in sufficient quantity to product an average 7.2 adduct number ethoxylate. Results are provided in the following table.

| Active Hydrogen Containing Compound | Mean Average Adduct Number | Peak Maximum |
| --- | --- | --- |
| Guerbet Alcohol | 4.0 | 7.9 |
| Ethylene Glycol | 3.2 | 60.1 |
|  | 2.0 | 38.3 |
| NEODOL 23 Alcohol | 6.8 | 24.0 |
| ALFOL 1412 Alcohol | 6.8 | 24.4 |
| Nonylphenol | 7.2 | 21.4 |

EXAMPLE 11

This example illustrates another series of ethoxylation reactions of different active hydrogen compounds, using a lanthanum phosphate catalyst.

The catalyst for these ethoxylation reactions was prepared in a manner similar to that of example 10. Small portions of lanthanum carbonate were added to a 2% aqueous solution of phosphoric acid at 70° C. over a 30 minute period. After all $CO_2$ evolution had ceased, the reaction slurry was heated at 100° C. for 2 hours, cooled to 25° C. and filtered. The filtrate was washed with deionized water until the wash water was neutral and then reslurried in deionized water. The slurry was treated with addition of dilute aqueous ammonium hydroxide to raise pH to 10, stirred at 25° C. for 4 minutes, and filtered to recover solids. The solids were washed with deionized until wash water was neutral, then dried under vacuum at 80° C. to recover white, free-flowing powder.

The lanthanum phosphate thus prepared was used to catalyze several ethoxylation reactions. Each reaction was carried our according to the general procedures of Example 1.

Reaction of a primary, substantially linear dodecyl mercaptan resulted in a product having a mean average adduct number of about 6 and a maximum in the adduct distribution curve at 28.6% w. The product contained 12% w polyethylene glycols as byproducts.

Reaction of a tertiary (propylene tetramer) thiol with ethylene oxide in the presence of lanthanum phosphate resulted in a product which contained significant quantities of unreacted thiol and thus considerable odor. To promote activity in the reaction of a tertiary thiol, another experiment was carried out in which the starting material was first converted to a "seed" tertiary thiol ethoxylate having a mean average adduct number of one. This seed ethoxylate was prepared by a potassium hydroxide catalyzed ethoxylation of tertiary (propylene tetramer) thiol. The product of the preliminary seed ethoxylation was neutralized with phosphoric acid and steam stripped to remove volatile materials which, if not removed, were found to poison the lanthanum phosphate catalyst. The seed ethoxylate was then reacted with further ethylene oxide in the presence of the lanthanum phosphate to produce a product having a mean average adduct number of about 6 and a maximum in the adduct distribution curve at 24% w. The product contained 10% w polyethylene glycols as byproducts.

Direct reaction of a mixture of $C_{11}$ and $C_{12}$, essentially linear secondary alcohols with ethylene oxide catalyzed by lanthanum phosphate was slow and resulted in a product having a relatively broad distribution of ethylene oxide adducts. When the secondary alcohols were first converted to a "seed" ethoxylate by a potassium hydroxide catalyzed addition of an average of about one mol of ethylene oxide, lanthanum phosphate catalyzed the reaction of the seed to a secondary alcohol ethoxylate having an average adduct number of about 7.5, a maximum peak in the ethylene oxide distribution curve of about 19% w and a polyethylene glycol content of about 1.9% w.

Reaction of a nonylphenol ethoxylate with ethylene oxide in the presence of the lanthanum phosphate resulted in a product having a mean average adduct number of about 6.5 and a distribution curve peak of 21%. Polyethylene glycol content was 6% w.

A lanthanum phosphate catalyzed ethoxylation of dodecaneoic acid (lauric acid) consumed only small quantities of EO at 140°–170° C. over 2 hours.

Ethoxylation of glycolic acid consumed an average of 1.1 mols of ethylene oxide per mole of acid over a three hour period. Because of the high melting point (80° C.) of the glycolic acid, it was, in this case, ethoxylated as a 30% w solution in diglyme.

The glycolic acid was also ethoxylated in molten form. The solid acid was added to the autoclave reactor and melted prior to introduction of ethylene oxide. Initially the ethoxylation proceeded rapidly, but rate slowed. The reaction did not proceed beyond a mean average adduct number of 2.5.

Reaction of ethylene glycol with two mols of ethylene oxide per mol of ethylene glycol produced a product having a peak maximum in the distribution curve (at triethylene glycol) of 39% w, and only 3% unreacted glycol.

EXAMPLE 12

A series of rare earth metal phosphates were prepared from the metal nitrate salts and phosphoric acid. In each case, about 10 millimols of the metal nitrate salt was dissolved in 50 ml of deionized water. To this solution was then added dropwise with rapid stirring about 11 millimols of phosphoric acid in 10 ml deionized water (a molar ratio of acid to metal of 1.1:1.0). The resulting mixture was stirred for one hour at room temperature and then neutralized with a 10N sodium hydroxide solution. After an additional hour of stirring, a solid phosphate salt product was isolated by filtration or centrifugation. The solid was washed several times with fresh deionized water and then dried first in air and finally under vacuum.

Each of the phosphate salts thus prepared were tested as catalyst for the ethoxylation of NEODOL 23 Alcohol, under the general procedures of Example 1 at temperatures in the range from 155° C. to 170° C. Results of each of the ethoxylation reactions are reported in the following table, in terms of the mean average adduct number for the product ethoxylate and the "peak maximum" for the ethylene oxide adduct distribution curve, i.e., the plot of % w for each individual adduct number vs. the adduct number. Peak maximum represents the % w concentration of the adduct number product species which is present in the greatest % w concentration.

| Catalyst | Mean Average Adduct Number | Peak Maximum |
| --- | --- | --- |
| yttrium phosphate | 6.4 | 16.2 |
| lanthanum phosphate | 6.9 | 22.8 |
| cerium phosphate | 7.0 | 23.0 |
| praseodymium phosphate | 7.2 | 19.3 |
| neodymium phosphate | 7.2 | 23.2 |
| samarium phosphate | 7.2 | 20.1 |
| europium phosphate | 7.9 | 17.4 |
| gadolinium phosphate | 6.2 | 16.4 |
| terbium phosphate | 6.9 | 16.1 |
| dysprosium phosphate | 6.2 | 15.1 |
| erbium phosphate | 6.5 | 15.8 |
| thulium phosphate | 6.3 | 15.9 |
| ytterbium phosphate | 6.2 | 15.4 |
| lutetium phosphate | 0.3 | 11.0 |

What is claimed is:

1. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of one or more of the phosphate salts of the rare earth elements having a formula $LPO_4$, $L_3(PO_4)_2$ or $L_3(PO_4)_4$, wherein L represents a rare earth element.

2. The process of claim 1, wherein the alkylene oxide reactant consists essentially of one or more alkylene oxides selected from the group consisting of ethylene oxide and propylene oxide.

3. The process of claim 2, wherein the active hydrogen containing reactant consists essentially of one or more compounds selected from the group consisting of alcohols, phenols and polyols, wherein the active hydrogen moiety is attached to a primary carbon atom.

4. The process of claim 3, wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

5. The process of claim 4, wherein the active hydrogen containing reactant consists essentially of one or more $C_1$-$C_{30}$ primary mono-hydric alkanols.

6. The process of claim 5, wherein the active hydrogen containing reactant consists essentially of primary mono-hydric alkanols having carbon numbers in the range from 6 to 24, inclusive, and the alkylene oxide reactant consists essentially of ethylene oxide.

7. The process of claim 6, wherein the active hydrogen containing reactant consists essentially of primary mono-hydric alkanols having carbon numbers in the range from 8 to 20, inclusive.

8. The process of claim 7, wherein greater than about 50% of the molecules of the primary mono-hydric alkanols are of linear carbon structure.

9. The process of claim 8, wherein greater than about 70% of the molecules are of linear carbon structure.

10. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of one or more of the phosphate salts having a formula $LPO_4$, $L_3(PO_4)_2$ or $L_3(PO_4)_4$, wherein L is selected from the group consisting of lanthanum, cerium, praseodymium, neodymium, samarium, gadolinium, dysprosium, erbium and ytterbium.

11. The process of claim 10, wherein the alkylene oxide reactant consists essentially of one or more alkylene oxides selected from the group consisting of ethylene oxide and propylene oxide.

12. The process of claim 11, wherein the active hydrogen containing reactant consists essentially of one or more compounds selected from the group consisting of alcohols, phenols and polyols, wherein the active hydrogen moiety is attached to a primary carbon atom.

13. The process of claim 12, wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

14. The process of claim 13, wherein the active hydrogen containing reactant consists essentially of one or more $C_1$-$C_{30}$ primary mono-hydric alkanols, and the alkylene oxide reactant consists essentially of ethylene oxide.

15. The process of claim 14, wherein the active hydrogen containing reactant consists essentially of primary mono-hydric alkanols having carbon numbers in the range from 6 to 24, inclusive.

16. The process of claim 15, wherein the active hydrogen containing reactant consists essentially of primary mono-hydric alkanols having carbon numbers in the range from 8 to 20, inclusive.

17. The process of claim 16, wherein greater than about 50% of the molecules of the primary monohydric alkanols are of linear carbon structure.

18. The process of claim 17, wherein greater than about 70% of the molecules are of linear carbon structure.

19. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of yttrium having the formula $YPO_4$.

20. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element cerium having the formula $CePO_4$.

21. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element praseodymium having the formula $PrPO_4$.

22. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element neodymium having the formula $NdPO_4$.

23. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element samarium having the formula $SmPO_4$.

24. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element gadolinium having the formula $GdPO_4$.

25. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element dysprosium having the formula $DyPO_4$.

26. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element erbium having the formula $ErPO_4$.

27. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the phosphate salt of the rare earth element ytterbium having the formula $YbPO_4$.

28. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of the rare earth element lanthanum having the formula $LaPO_4$.

29. The process of any of claims 19, 20, 21, 22, 23, 24, 25, 26, 27 and 28, wherein the alkylene oxide reactant consists essentially of one or more alkylene oxides selected from the group consisting of ethylene oxide and propylene oxide, and wherein the active hydrogen containing reactant consists essentially of one or more compounds selected from the group consisting of alcohols, phenols and polyols, wherein the active hydrogen moiety is attached to a primary carbon atom.

30. The process of claim 28, wherein the active hydrogen containing reactant consists essentially of primary mono-hydric alkanols having carbon numbers in the range from 6 to 24, inclusive, and the alkylene oxide reactant consists essentially of ethylene oxide.

31. The process of claim 29, wherein the active hydrogen containing reactant consists essentially of primary mono-hydric alkanols having carbon numbers in the range from 8 to 20, inclusive, wherein greater than about 70% of the primary mono-hydric alkanol molecules are of linear carbon structure.

32. The process of claim 28, wherein the active hydrogen-containing reactant consists essentially of polyols having from 2 to about 6 hydroxyl groups and the alkylene oxide reactant consists essentially of propylene oxide.

33. The process of claim 1, wherein the alkylene oxide reactant consists essentially of ethylene oxide.

34. The process of claim 32, wherein the active hydrogen-containing reactant consists essentially of one or more primary mono-hydric alkanols having carbon numbers in the range from 8 to 20, inclusive.

35. The process of claim 1, wherein the active hydrogen-containing reactant consists essentially of polyols having from 2 to about 6 hydroxyl groups and the alkylene oxide reactant consists essentially of one or more alkylene oxides selected from the group consisting of propylene oxide and ethylene oxide.

36. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds wherein the active hydrogen moiety is attached to a primary carbon atom, in the presence of a catalytically effective amount of at least two of the phosphate salts selected from the group consisting of those having the formula $L(PO_4)$ wherein L is selected from the group consisting of yttrium, lanthanum, cerium, praseodymium, neodymium, samarium, gadolinium, dysprosium, erbrium and ytterbium.

37. The process of claim 35, carried out in the presence of a catalytically effective amount of the phosphate salts of a mixture of rare earth elements selected from the group consisting of bastnasite, monazite, xenotime, didymium, gadolinite and euxenite.

38. The process of claim 36, wherein the active hydrogen-containing reactant consists essentially of one or more primary mono-hydric alkanols having carbon numbers in the range from 8 to 20, inclusive, and the alkylene oxide reactant consists essentially of ethylene oxide.

39. The process of either of claim 36, wherein the active hydrogen-containing reactant consists essentially of polyols having from 2 to about 6 hydroxyl groups and the alkylene oxide reactant consists essentially of propylene oxide, ethylene oxide or mixtures thereof.

40. A process for the preparation of ethylene oxide adducts of higher alkanols, which comprises contacting and reacting ethylene oxide with one or more $C_8$ to $C_{20}$ primary mono-hydric alkanols in the presence of a catalytically effective amount of one or more of the phosphate salts having the formula $LPO_4$, wherein L is an element of the lanthanum series.

41. The process of claim 39, wherein greater than about 50% of the alkanol molecules are of linear carbon structure.

42. The process of claim 40, carried out in the presence of a catalytically effective amount of one or more of the phosphate salts of the elements selected from the group consisting of lanthanum, cerium, neodymium, and praseodymium.

43. The process of any of claims 1, 10, 35, 39, and 40, carried out in the presence of a catalytically effective amount of one or more phosphate salts having hexagonal crystal structure.

44. The process of claim 42, wherein the phosphate salts have a water content of at least 5 percent by weight.

45. The process of either of claims 39 and 40, wherein the phosphate salts have a water content of at least 5 percent by weight.

* * * * *